United States Patent

Arndt et al.

Patent Number: 4,552,970
Date of Patent: Nov. 12, 1985

[54] SOLVATED SALTS OF DINITROPHENYLCYANAMIDES, AND A PROCESS FOR THE PREPARATION THEREOF

[75] Inventors: Otto Arndt, Hofheim am Taunus; Theodor Papenfuhs, Frankfurt am Main; Wolfgang Tronich, Eppstein/Taunus, all of Fed. Rep. of Germany

[73] Assignee: Hoechst Aktiengesellschaft, Frankfurt am Main, Fed. Rep. of Germany

[21] Appl. No.: 576,168

[22] Filed: Feb. 1, 1984

Related U.S. Application Data

[63] Continuation of Ser. No. 328,484, Dec. 8, 1981, abandoned.

[30] Foreign Application Priority Data

Dec. 10, 1980 [DE] Fed. Rep. of Germany ....... 3046490

[51] Int. Cl.[4] .................. C07C 125/08; C07C 127/19
[52] U.S. Cl. ...................................... 548/543; 564/50; 564/105; 548/555; 549/87
[58] Field of Search ................ 564/105; 548/543, 555; 549/87

[56] References Cited

U.S. PATENT DOCUMENTS 3,692,832  9/1972  Rider .................................... 564/105
4,206,141  6/1980  Mihailovski .................... 564/105 X
4,281,187  7/1981  Papenfuhs et al. .................... 564/50

FOREIGN PATENT DOCUMENTS

EP53714  6/1982  European Pat. Off. .

OTHER PUBLICATIONS

Giua et al., CA 20:173[5] (1926).

*Primary Examiner*—Thomas A. Waltz
*Attorney, Agent, or Firm*—Curtis, Morris & Safford

[57] ABSTRACT

Compounds of the formula I

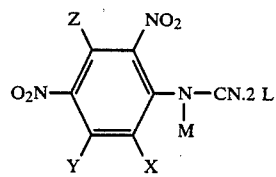

in which X denotes hydrogen, fluorine, chlorine or bromine, Y and Z denote hydrogen, lower alkyl or lower alkoxy, M denotes sodium, potassium or one equivalent of calcium and L denotes a dipolar aprotic solvent, are obtained from compounds of the formula II

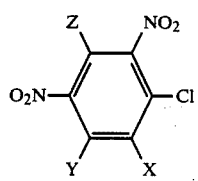

in which X, Y and Z have the abovementioned meanings, and a metal cyanamide of the formula III

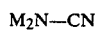

in which M has the abovementioned meaning, in a dipolar aprotic solvent, which after the reaction is substantially removed, whereupon a lower molecular weight aliphatic alcohol is added to the residue and the product precipitated is isolated. Nitrophenylureas of the formula IV

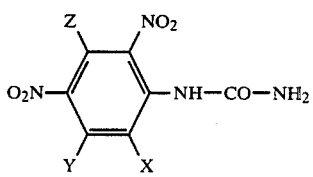

in which X, Y and Z have the abovementioned meanings, are obtained from the compounds of the formula I by acid hydrolysis.

3 Claims, No Drawings

SOLVATED SALTS OF DINITROPHENYLCYANAMIDES, AND A PROCESS FOR THE PREPARATION THEREOF

This application is a continuation application of Ser. No. 328,484 filed Dec. 8, 1981 and now abandoned.

The invention relates to compounds of the formula

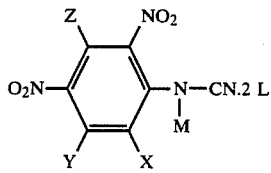

in which X denotes hydrogen, fluorine, chlorine or bromine, Y and Z denote hydrogen, lower alkyl or lower alkoxy, M denotes sodium, potassium or one equivalent of calcium and L denotes a dipolar aprotic solvent.

Those compounds of the formula I are preferred, in which X denotes hydrogen or in particular chlorine, Y and Z denote methyl, methoxy or in particular hydrogen, M denotes sodium or in particular one equivalent of calcium, and L denotes tetramethylene sulfone or in particular N-methylpyrrolidone or dimethyl sulfoxide.

The invention also relates to a process for the preparation of the compounds I from compounds of the formula II

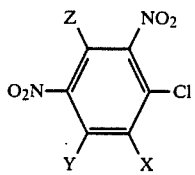

in which X, Y and Z have the abovementioned meanings, and cyanamide in a polar solvent, which process comprises using the cyanamide in the form of a metal cyanamide of the formula III

M$_2$N—CN in which M has the abovementioned meaning, and using a dipolar aprotic solvent as the polar solvent, which is substantially removed after the reaction, whereupon a low molecular weight aliphatic alcohol is added to the residue and the product precipitated is isolated.

The invention also relates to the use of the compounds of the formula I for the preparation of dinitrophenylureas of the formula IV

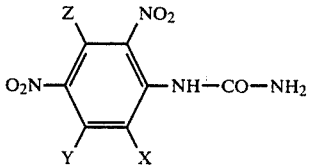

in which X, Y and Z have the abovementioned meanings, by hydrolysis. This produces highly pure ureas.

It is known, from J. pract. Chem. [2] 110 (1925) 300, to react 2,4-dinitrochlorobenzene with a large excess of cyanamide in aqueous ethanol to give 2,4-dinitrophenylcyanamide and to precipitate the latter by means of hydrochloric acid. When this precipitate is heated together with alcoholic hydrochloric acid, 2,4-dinitrophenylurea is obtained therefrom.

U.S. Pat. No. 3,979,453 discloses the reaction of N-substituted 3-chloro-2,6-dinitro-4-trifluoromethylanilines with cyanamide in the presence of a strong base in inert solvents, such as ethanol, dioxane or tetrahydrofuran. After cooling, the reaction solution is poured onto ice water and the product precipitated is recrystallized from ethanol and water.

German Offenlegungsschrift No. 2,855,882 (=U.S. Pat. No. 4,281,187) describes that it is possible to react 2,4-dinitro-1-chlorobenzene with cyanamide in an aqueous medium to give 2,4-dinitrophenylcyanamide and to hydrolyze this by acid hydrolysis, without isolating it first, to give 2,4-dinitrophenylurea.

In contrast to these known preparation methods, the process according to the invention does not start with free cyanamide, but it starts from metal salts which are obtained by the customary industrial processes, in particular from calcium cyanamide, which is preferably used in the form of technical lime nitrogen. This produces compounds of the formula I, which can be isolated in a crystalline form and which, on being hydrolyzed, produce the corresponding ureas in high purity.

Preferred embodiments of the invention are explained in greater detail below.

The reaction is preferably carried out at temperatures of about 25° to about 90° C., especially about 50° to about 70° C.

Solvents which can be used as the dipolar solvent are acetonitrile, dimethylformamide, dimethylacetamide, tetramethylene sulfone and in particular dimethyl sulfoxide and N-methylpyrrolidone.

The reaction rate can be increased by the addition of small amounts of cyanamide, which is advantageously used in the form of the commercially available crystalline form. The amount is about 0.1 to about 0.25 mole per mole of metal cyanamide, which in turn is advantageously used in an excess of about 10 to about 80%. A total of about 1.5 moles of cyanamides (sum of metal cyanamide and free cyanamide) are preferably chosen per mole of a compound of the formula II.

Since it is possible, under the reaction conditions, for a compound of the formula II to form the corresponding phenol by a reaction with water, the reaction is preferably carried out with the exclusion of water and—in contrast to the known processes—without the addition of a base.

The course of the reaction can be monitored by taking samples and evaluating them by thin layer chromatography, the end of the reaction being indicated by the disappearance of the starting component of the formula II.

After the reaction is complete, the solid constituents (excess metal cyanamide, and, when lime nitrogen has been used, in addition calcium oxide and carbon) are removed from the reaction mixture and the dipolar aprotic solvent is removed substantially, preferably by a distillation in vacuo. The low-molecular aliphatic alcohol is added to the residue of the distillation, the solvated salt of the formula I being precipitated. Approximately the 4-fold amount by weight of isopropanol, relative to the starting material of the formula II, is advantageously added. The salt of the formula I which precipitates in a crystalline form can be further processed in this form, but advantageously it is separated off, for example by filtration, and washed with a low-molecular alcohol, in particular with the alcohol used for the precipitation, and it is then either further processed in this form or, advantageously, dried, since this produces particularly pure ureas.

The hydrolysis of the compounds of the formula I to give the ureas of the formula IV is carried out in an acid medium. For this purpose, the salt of the formula I is advantageously dissolved in an aqueous mineral acid and the solution is diluted by the addition of water until the free cyanamide precipitates. This is then hydrolyzed, in an aqueous suspension, at temperatures of 15° to 80° C., preferably 50° to 70° C.

The resulting urea of the formula IV can be subjected directly to further processing. However, it is advantageously washed with water, then with a sodium bicarbonate solution until it has a neutral reaction and then again with water. The moist product thus obtained can be further processed without drying, for example in accordance with German Offenlegungsschrift No. 2,855,883 (=U.S. Pat. No. 4,246,196) to give the corresponding 5-aminobenzimidazolone. However, the urea can also be dried, for example at about 60° C. in vacuo. The 2,4-dinitrophenylureas of the formula IV are obtained in a very pure form and they contain only very small amounts of the corresponding 2,4-dinitroanilines.

In the Examples below, data in parts and percentages are by weight, unless otherwise indicated.

EXAMPLES 1. 474 parts (2 moles) of 1,2-dichloro-3,5-dinitrobenzene are stirred in 4,740 parts of N-methylpyrrolidone together with 343 parts of 63% pure lime nitrogen (2.7 moles) and 13 parts of crystalline 98% pure cyanamide (0.3 mole) for 15 hours at 60° C. The residual lime nitrogen is separated off and washed with 200 parts of N-methylpyrrolidone. The combined filtrates are concentrated under a vacuum of up to 5 mbar at temperatures of up to 85°–87° C. The residue of the distillation is taken up in 1,600 parts of isopropanol. The calcium salt of 6-chloro-2,4-dinitrophenylcyanamide, solvated with 2 moles of N-methylpyrrolidone, which crystallized out at 40° C., is filtered off at 10° C., washed with isopropanol and dried in vacuo at 50° C.

773 parts of a crystalline product of melting point 114° C. are obtained, which corresponds to a yield of 84%. An elementary analysis corresponds to the formula $C_{17}H_{20}ClN_6O_6Ca_{0.5}$ (molecular weight 459.9).

The structure was confirmed by nuclear magnetic resonance.

773 parts of the dried calcium salt ($\times 2$ NMP) are dissolved in 4,900 parts of 30% strength hydrochloric acid at 5°–10° C. The solution is diluted with 2,000 parts of water. The 6-chloro-2,4-dinitrophenylcyanamide which then crystallizes out is hydrolyzed at 60° C. to give 6-chloro-2,4-dinitrophenylurea, which is filtered off and then washed successively with water, 5% strength sodium bicarbonate solution and again with water. After drying, 428 parts of pure, light yellow 6-chloro-2,4-dinitrophenylurea, which has crystallized in the form of needles and has a melting point of 220°–225° C., are obtained, which corresponds to a yield of 98%, relative to the calcium salt, and 82%, relative to 1,2-dichloro-3,5-dinitrobenzene.

2. 474 parts (2 moles) of 1,2-dichloro-3,5-dinitrobenzene, 343 parts of 63% pure lime nitrogen (2.7 moles) and 13 parts of crystalline 98% pure cyanamide (0.3 mole) are stirred in 4,740 parts of dimethyl sulfoxide for 7 hours at 60° C. The working-up procedure of Example 1 is followed.

After drying, 752 parts of the calcium salt of 6-chloro-2,4-dinitrophenylcyanamide, solvated with 2 moles of dimethyl sulfoxide, are obtained, which corresponds to a yield of 90%. Melting point 165° C. An elementary analysis corresponds to the formula $C_{11}H_{14}ClN_4O_6S_2Ca_{0.5}$ (molecular weight 417.9).

The structure was confirmed by NMR.

Hydrolysis is hydrochloric acid, in accordance with Example 1, produces from 752 parts of the dried calcium salt ($\times 2$ DMSO), 450 parts of pure 6-chloro-2,4-dinitrophenylurea, which corresponds to a yield of 97%, relative to the calcium salt, and 86%, relative to 1,2-dichloro-3,5-dinitrobenzene. Melting point=220°–225° C. As in Example 1 the urea forms needles, which retain only a small amount of mother liquor (about 200 parts) and have good filtering properties. Surface area (by the Stroöhlein method) is about 0.6 $m^2/g$.

3. The procedure of Example 1 and 2 is followed, but tetramethylene sulfone (TMSO) is used as the solvent. The reaction in TMSO requires a higher temperature of 80°–90° C.

The yield corresponds to the yields obtained in Example 1 and 2.

4. The procedure described in Example 2 is followed, but 900 parts of isopropanol-moist calcium salt, with a solids content of 752 parts, are used in the hydrolysis. A urea is obtained, which has considerably finer crystals than the urea of Example 2 and whose surface area (by the Stroöhlein method) is about 20 $m^2/g$.

The urea retains a lot of mother liquor (about 900 parts) during the filtration, which slows down the latter and makes washing more difficult. The product is contaminated to a small extent with 6-chloro-2,4-dinitroaniline (to the extent of 1–2% as measured by HPLC) and it has a melting point of 215°–220° C.

5. The procedure of Example 2 is followed, but 150 parts of isopropanol are added to the hydrochloric acid. The result is the same as in Example 2.

6. The procedure of Example 2 is followed, but the isopropanol-moist calcium salt is not dried, but it is dissolved in the 4-fold amount by weight of water. The aqueous, slightly alkaline solution runs into the 30% strength hydrochloric acid. The 6-chloro-2,4-dinitrophenylurea thus obtained is markedly contaminated with 6-chloro-2,4-dinitroaniline ($>2\%$).

7. The procedure of Example 1 is followed, but with the difference that instead of lime nitrogen, 258 parts of pulverulent disodium cyanamide (3 moles) and 32 parts of crystalline 98% pure cyanamide (0.75 mole) are employed. The cyanamide is added in 2 parts, in that a quarter is only added towards the end of the reaction. The reaction takes 28 hours at 60° C. Thereafter, N-methylpyrrolidone is distilled off. The residue from the distillation is taken up in 1,600 parts of isopropanol and mixed with 2,450 parts of 30% strength hydrochloric acid, the mixture is heated to 60° C. and stirring is continued at this temperature for 3 hours. The isolation of 6-chloro-2,4-dinitrophenylurea is effected as in Example 1.

8. 81 parts of 2,4-dinitrochlorobenzene, 69 parts of 63% pure lime nitrogen (0.54 mole) and 2.6 parts of crystalline 98% pure cyanamide (0.06 mole) are stirred for 22 hours at 80° C. in 800 parts of dimethyl sulfoxide. The residual lime nitrogen is separated off and washed with 80 parts of dimethyl sulfoxide. The combined filtrates are concentrated under a vacuum of up to 5 mbar at a temperature of up to 70° C. The residue from the distillation is taken up in 300 parts of isopropanol. The calcium salt of 2,4-dinitrophenylcyanamide, solvated with 2 moles of dimethyl sulfoxide, which crystallizes out at 47° C., is filtered off at 10° C., washed with isopropanol and dried in vacuo at 50° C.

128 parts of a crystalline product which has a melting point of 113°–115° C., are obtained, which corresponds to a yield of 84% of theory. An elementary analysis corresponds to the formula $C_{11}H_{15}N_4O_6S_2Ca_{0.5}$ (molecular weight 383.4). The structure was confirmed by nuclear magnetic resonance.

We claim:

1. A solid crystalline solvated salt of the formula

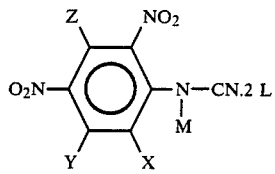

wherein
X is hydrogen, fluorine, chlorine, or bromine;
Y and Z are hydrogen, lower alkyl, or lower alkoxy;
M is sodium, potassium, or one molar equivalent of calcium; and
L is a dipolar aprotic solvent.

2. A solid crystalline solvated salt as in claim 1 wherein X is hydrogen or chlorine;
Y and Z are hydrogen, methyl or methoxy;
M is sodium or one molar equivalent of calcium; and
L is tetramethylene sulfone, N-methyl-pyrrolidone, or dimethyl sulfoxide.

3. A compound as in claim 2 wherein X is chlorine;
Y and Z are hydrogen; and
M is one molar equivalent of calcium.

* * * * *